United States Patent [19]

Kümin et al.

[11] Patent Number: 5,849,551
[45] Date of Patent: Dec. 15, 1998

[54] MICROBIOLOGICAL PROCESS FOR PRODUCING γ-DECALACTONE

[75] Inventors: Bruno Kümin, Dübendorf; Thomas Münch, Illnau, both of Switzerland

[73] Assignee: Givaudan-Roure (International) SA, Vernier-Genéve, Switzerland

[21] Appl. No.: 814,074

[22] Filed: Mar. 10, 1997

[30] Foreign Application Priority Data

Mar. 15, 1996 [EP] European Pat. Off. ............... 96104111

[51] Int. Cl.[6] ............................. C12P 17/04; C12P 17/06
[52] U.S. Cl. ........................... 435/126; 435/125; 435/931
[58] Field of Search .................................... 435/125, 126, 435/931, 131

[56] References Cited

U.S. PATENT DOCUMENTS 5,032,513  7/1991  Page et al. ............................. 435/125

FOREIGN PATENT DOCUMENTS

WO 89/12104  12/1987  WIPO .

*Primary Examiner*—Herbert J. Lilling
*Attorney, Agent, or Firm*—George W. Johnston; Alan P. Kass; Mark E. Waddell

[57] ABSTRACT

A microbiological process for the production of γ-decalactone. According to this process, a culture of the fungus of a particular species of the genus Mucor is incubated with the particular substrate, which is an organic carboxylic acid ester, to produce fermentatively the γ-decalactone. Exact conditions have now been discovered under which γ-decalactone can be prepared in high yields. These conditions are based upon the fermentative incubation of a fungus of the genus Mucor in conjunction with the appropriate substrate in order to obtain the high yield of the desired lactone.

5 Claims, No Drawings

MICROBIOLOGICAL PROCESS FOR PRODUCING γ-DECALACTONE

FIELD OF INVENTION

The present invention concerns a microbiological process for the production of γ-decalactone. According to this process, a culture of the fungus of a particular species of the genus Mucor is incubated with a particular substrate, which is an organic carboxylic acid ester, to produce fermentatively the γ-decalactone.

BACKGROUND OF INVENTION

The microbiological process for the manufacture of γ and δ lactones using, inter alia, the microorganism Mucor is known, see WO 89/12104 of Dec. 14, 1987. In as far as the material γ-decalactone is concerned, Example 2 of this publication gives no recoverable, but only trace amounts. Furthermore, Example 1 is silent in this respect, in as far as no yields for the concentration of the product in the fermentation broth, i.e. the reaction mixture, are given.

SUMMARY OF INVENTION

In particular, the novel microbiological process for the production of γ-decalactone comprises incubating first in a nutrient broth a culture of a fungus of the species Mucor circinelloides wherein, preferably, the incubation period is about 5 to about 30 hours, then adding the substrate ethyl decanoate, and wherein this substrate is continuously added at a feed rate of from about 2 g to about 3 g per hour per liter of nutrient broth, and the substrate concentration in the nutrient broth being from about 0.1% to about 1.5% by weight, relative to the total weight of the nutrient broth, and, this microbiological process then being followed by a lactonization of the primary reaction product in a manner known per se.

The nutrient broth used according to the process of the invention includes preferred sources of nitrogen, carbohydrates, minerals and oxygen. Incubative fermentation conditions used according to the process include any pH, temperature, substrate concentration and substrate feed rate, which will maintain the viability and productivity of the culture.

The inventive process may be conducted in a batch or continuous mode of operation. In the preferred batch fermentation, the nutrient broth, microbial culture and substrate are combined and fermented until the concentration of the product, i.e. the γ-hydroxy decanoic acid and the lactone respectively becomes constant.

DETAILED DESCRIPTION

The microbiological process of the invention is useful for the production, in a high yield, of the optically active γ-decalactone from an organic carboxylic acid ester; the corresponding lactone produced will have the formula

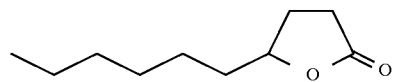

wherein primarily the (R) enantiomer of the corresponding lactone is involved.

Such lactone is a flavor and fragrance compound. By including effective amounts of this lactone produced according to this invention, it is possible to augment or enhance the organoleptic properties of consumables such as beverages, chewing gums, fruit juices, tobacco products, pharmaceutical preparations, perfumes, perfumed products and the like. This lactone is especially valuable in certain flavor compositions where wholly natural ingredients are required.

According to the invention, exact conditions have now been discovered under which γ-decalactone can be prepared in high yields. These conditions are based upon the fermentative incubation of a fungus of the genus Mucor in conjunction with the appropriate substrate in order to obtain the high yield of the desired lactone.

Suitable are, as pointed out above, the species Mucor circinelloides, e.g. the strains DSM 10473 which were deposited on Dec. 1, 1996 at the German Depository Authority DSM, "Deutsche Sammlung von Mikroorganismen und Zellkulturen GmbH" at Mascheroder Weg 1b, D-38124 Braunschweig under the Budapest Treaty on the International Recognition of the Deposit of Microorganisms for Patent Purposes and the known strains DSM 1175, 1173 and 2183, etc. of this filamentous fungus.

Strains DSM 1175, 1173 and 2183 are also on deposit at the German Depository referenced above under the Budapest Treaty. These strains are readily available to the public as they are listed in the "Catalogue of Strains 1993" available from "DSM-Deutche Sammlung von Mikroorganismen und Zellkulturen GmbH" at Mascheroder Weg 1b, D-38124 Braunschweig.

Preferred are the strains DSM 10473 and 1175.

The identity of Mucor circinelloides DSM 10473 of Dec. 1, 1996 was determined by examining the morphological and physiological characteristics. Besides microscopic observations, biochemical standard reactions for strains characterization were carried out.

Thus:

When growing in surface cultures (e.g. YM agar, good growth (i.e. the Yeast maltose agar surface is covered after 1–2 days of incubation with a mycelia layer) and sporulation at 5°–30° C.), Mucor circinelloides DSM 10473 forms initially grayish, later more olive-green colonies up to 6–8 mm in height, composed of tall and short sporangiophores with 10–15 μm in diameter. The sporangiophores are repeatedly sympodically branched with long and short branches, the latter infrequently circinate. Short sporangiophores are more profusely branched with short and often circinate branches and have slightly incrusted walls. Younger parts of sporangiophores are filled with droplets. At low temperatures (5° C.), sporangiophores become shorter and heavily branched. Sporangia are first off-white to yellow, become brownish-grey when mature and have a size of 80–100 μm in diameter. Columellae are 20–40 μm in diameter, ellipsoidal in larger sporangia and more globose in smaller sporangia, the color is greyish-brown. The smother-walled sporangiospores are slightly ellipsoidal, rarely globose and with a diameter of 3–6 μm. Only few chlamydospores occur in and on the substrate. Zygospores are orange-brown to dark brown, globose and slightly compressed and up to 100 μm in diameter.

The substrate utilized is defined by the formula

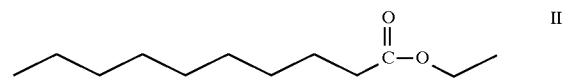

In carrying out the present invention, cultivation and fermentative incubation of the fungus are accomplished in an aqueous medium in the presence of the usual nutrient substances. A suitable medium is one which contains carbon sources, nitrogen sources, inorganic salts and growth factors. Among the suitable carbon sources are, for example, glucose (preferred), fructose, xylose, sucrose, maltose, lactose, mannitol, sorbitol, glycerol, corn syrup and corn syrup solids. Examples of suitable nitrogen sources include organic and inorganic nitrogen-containing substances such as peptone, corn steep liquor (preferred), meat extract, yeast extract (preferred), casein, urea, amino acids, ammonium salts, nitrates and mixtures thereof. Examples of inorganic salts include phosphates, sulfates, magnesium, sodium, calcium, and potassium ions. These nutrients may be supplemented with, for example, one or more vitamins of the B group.

For the nutrient broth, it is preferred to utilize dextrose at a concentration of about 1 to about 20 weight percent, more preferably about 4 to about 12 weight percent, and most preferably about 8 to 12 weight percent.

In the preferred procedure, the Mucor fungus is first cultivated to produce a mature culture in the nutrient broth. The culture is inoculated into a fermentor containing nutrient broth in order to initiate the growth phase. The substrate is then added and fermentation continued.

The appropriate timing is as follows:

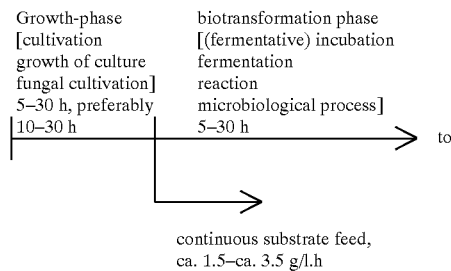

It is assumed that it is this timing and this substrate feed which is mainly responsible for the high product yield obtained.

The cultivation and fermentative incubation of the fungus can be carried out as a submerged culture (e.g., shake-flask, fermentor), most preferably under aerobic conditions. Cultivation and incubation suitably may proceed in a pH range of from about 3 to about 9, preferably in the range of from about 4 to about 9, and most preferably about. 6 to about 7. The pH should be regulated by the addition of an inorganic or organic acid or base, such as hydrochloric acid, acetic acid, sodium hydroxide, calcium carbonate, ammonia, etc. The incubation temperature is suitably maintained at between about 18° C. and about 35° C., with a range from about 20° C. to about 30° C. being preferred, and a range from about 25° C. to about 30° C. being especially preferred.

The substrate may be added either alone or in combination with a carbon source, such as glucose, namely when the growth phase is complete. It is preferable to add the substrate to the culture medium during the period of from 5 up to 30 hours after the growth phase of the culture in the fermentation broth. Desirable results can be obtained when the substrate is added continuously over the entire biotransformation phase after an initial fungal cultivation period of from 5 up to about 30 hours.

The suitable feed rate for this continuous addition is ca. 1.5 to 3.5 g per hour per liter of broth, more preferred ca. 2 to 3 g per hour per liter.

In practice, the concentration of the substrate in the medium may conveniently vary from 0.1% to about 1.5%, preferably about 0.5% to about 1%, by weight consistent with the manner in which it is added to the culture, i.e. consistent with the feed rate.

The reaction period varies primarily according to the feed rate. In general, the biotransformation phase takes between about 5 hours and about 30 hours, or longer, depending upon the microbial strain utilized.

The incubation is carried out under aerobic conditions, wherein the dissolved oxygen content in the fermentation broth is from 10 to 100% of the saturation concentration, preferably 30% to 80%. Also, preferably, the substrate is maintained in continuous contact with the aqueous phase and the microorganism. Generally, vigorous stirring is satisfactory. Conventional antifoam agents such as silicone oils, polyalkylene glycol derivatives, etc. can be used to control foaming.

The progress of the fermentative production of the γ-hydroxy acid and the lactone respectively can be monitored by assaying for lactone concentration using standard analytical techniques, such as chromatography (gas-liquid, thin layer or high pressure liquid). The fermentation can also be followed by measuring consumption of glucose, oxygen or by measuring pH changes.

After termination of the reaction, the reaction mixture is lactonized in a manner known for γ-hydroxy-acids, i.e. is conveniently acidified with acid, e.g. with phosphoric acid, to a pH value of about 1 to about 3, preferably of about 1.5 to about 2.5, and subsequently lactonized by heating. The heat treatment is conveniently carried out in a temperature range between about 60° to about 120° C., preferably at about 90° C., for about 10 to about 90 minutes, preferably about 20 to about 90 minutes.

The fermentation broth is microfiltrated and the rententate extracted with an organic solvent, such as an alcohol, e.g. ethanol, an ester, especially ethyl acetate, or an ether, such as methyl tert.butyl ether, according to known methods. Subsequently, the biomass is removed by separation and the solvent is conveniently removed by distillation.

If necessary, the purification of the final product of the present invention can be achieved by conventional techniques which include distillation, chromatographic separation, and the like.

The following example is set forth to more fully illustrate embodiments of the invention but is in no way meant to limit the scope thereof.

EXAMPLE 7 l of preculture of Mucor circinelloides (strain DSM 10473) was added to a fermenter containing 290 l of culture medium (containing 100 g/l of glucose, 20 g/l of yeast extract, 12 g/l of corn steep liquor +1 g/l $KH_2PO_4$+1 g/l Mg $SO_4·H_2O$). There followed a growth phase of 18 hours, at an aeration rate of 0.08 vvm of compressed air at pH 6.5, 28° C. under stirring with 175 rpm. The pH was brought to 7.5 by means of NaOH, the rate of aeration was doubled and 2.8 kg of ethyl caprinate were pumped into the fermenter during 30 minutes. There followed a feed of ethyl caprinate of 0.8 kg/hours during 13.2 hours. 42 hours after the inoculation of the fermenter the pH of the product was brought to 2.5 with $H_3PO_4$ (85%) and the temperature was brought to 90° C. for 25 minutes in order to lactonize the γ-hydroxy acid. The concentration of γ-decalactone was 10.5 g/l.

The fermentation liquid was microfiltrated (0.2 μm) and the retentate (i.e. the residue containing the product and the biomass) was extracted batch-wise with ethanol. The extract, which had been made cell-free by means of a separator, was concentrated, the residue, i.e. the product, was neutralized by means of aqueous NaOH and NaCl was added under agitation. An upper phase (containing the product) was separated and was extracted with MTBE (tert.butyl methyl ether). After solvent evaporation, the raw extract was flash distilled under vacuum. The distillate consisted of 40% of γ-decalactone and 60% ethyl caprinate.

The content of the γ-decalactone can further be increased by means of fine distillation.

The ethyl caprinate used in the Example can be of synthetic, of semi-natural or natural origin.

Analogous results were obtained when using the strain DSM 1175. The results using the strain DSM 1173 and DSM 2183 were slightly inferior.

We claim:

1. A microbiological process for the production of γ-decalactone, which comprises:
   a) incubating first in a nutrient broth a culture of a fungus of the species Mucor circinelloides,
   b) forcing a primary reaction product by adding the substrate ethyl decanoate, wherein this substrate is continuously added at a feed rate of from about 2 g to about 3 g per hour per liter of nutrient broth, leading to a substrate concentration in the nutrient broth being from about 0.1% to about 1.5% by weight, relative to the total weight of the nutrient broth, and
   c) then lactonizing the primary reaction product which is formed in step (b).

2. The process according to claim 1, wherein the incubation is conducted at a pH of about 3 to about 9, and at a temperature of about 18° C. to about 35° C.

3. The process according to claim 2, wherein the nutrient broth comprises:
   a) a yeast extract or cornsteep liquor at a concentration of about 0.05 to about 8% by weight relative to the total weight of the broth, and
   b) the carbohydrate dextrose at a concentration of about 1% to about 20% by weight relative to the weight of the broth.

4. The process according to claim 3, wherein the pH is about 4 to about 9, the temperature is about 20° C. to about 30° C., and the oxygen partial pressure is about 30% to about 80%.

5. A process according to claim 1 wherein the culture is incubated for a period of from about 5 to about 30 hours.

* * * * *

UNITED STATES PATENT AND TRADEMARK OFFICE
CERTIFICATE OF CORRECTION

PATENT NO : 5,849,551

DATED : December 15, 1998

INVENTOR(S) : BRUNO KUMIN, et al.

It is certified that error appears in the above-identified patent and that said Letters Patent is hereby corrected as shown below:

Column 5, line 15: Delete: "forcing" and Insert: "forming"

Signed and Sealed this

Eighteenth Day of May, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO.    : 5,849,551
DATED         : Dec. 15, 1998
INVENTOR(S)   : Bruno Kumin, et al It is certified that error appears in the above-identified patent and that said Letters Patent is hereby corrected as shown below:

Column 5, line 13, delete, "forcing" and insert --forming--

This Certificate supersedes Certificate of Correction issued May 18, 1999.

Signed and Sealed this

Fourteenth Day of September, 1999

Attest:

Q. TODD DICKINSON

Attesting Officer        Acting Commissioner of Patents and Trademarks